(12) United States Patent
Braun

(10) Patent No.: US 8,481,778 B2
(45) Date of Patent: Jul. 9, 2013

(54) PROCESS FOR THE PREPARATION OF ESTERS OF 4-FLUOROSUBSTITUTED 3-OXO-ALCANOIC ACIDS

(75) Inventor: Max Josef Braun, Wedemark (DE)

(73) Assignee: SOLVAY (Societe Anonyme), Brussels (BE)

( * ) Notice: Subject to any disclaimer, the term of this patent is extended or adjusted under 35 U.S.C. 154(b) by 37 days.

(21) Appl. No.: 12/673,030

(22) PCT Filed: Aug. 14, 2008

(86) PCT No.: PCT/EP2008/060674
§ 371 (c)(1),
(2), (4) Date: May 17, 2011

(87) PCT Pub. No.: WO2009/021987
PCT Pub. Date: Feb. 19, 2009

(65) Prior Publication Data
US 2011/0301378 A1    Dec. 8, 2011

(30) Foreign Application Priority Data

Aug. 16, 2007   (EP) .................................... 07114439

(51) Int. Cl.
*C07C 69/66* (2006.01)
(52) U.S. Cl.
USPC ...................................................... 560/174
(58) Field of Classification Search
None
See application file for complete search history.

(56) References Cited

U.S. PATENT DOCUMENTS

| | | | |
|---|---|---|---|
| 3,538,002 A | 11/1970 | Wilson | |
| 3,883,407 A | 5/1975 | Dittman | |
| 4,563,525 A | 1/1986 | Campbell | |
| 4,898,645 A | 2/1990 | Voigt et al. | |
| 5,010,154 A | 4/1991 | Hardiman | |
| 5,225,570 A | 7/1993 | Williams et al. | |
| 5,405,991 A | 4/1995 | Feist et al. | |
| 5,426,252 A | 6/1995 | Sherif | |
| 5,498,624 A | 3/1996 | McLoughlin et al. | |
| 5,545,298 A | 8/1996 | Braun et al. | |
| 5,569,782 A | 10/1996 | Braun et al. | |
| 5,750,810 A | 5/1998 | Schirmann et al. | |
| 6,252,105 B1 * | 6/2001 | Braun et al. | 560/227 |
| 6,525,213 B1 | 2/2003 | Braun et al. | |
| 6,706,911 B1 | 3/2004 | Lui et al. | |
| 7,026,521 B1 | 4/2006 | Mukhopadhyay et al. | |
| 7,057,079 B2 | 6/2006 | Braun et al. | |
| 7,405,328 B2 | 7/2008 | Hausmann et al. | |
| 7,501,527 B2 | 3/2009 | Lantzsch et al. | |
| 7,585,998 B2 * | 9/2009 | Gallenkamp et al. | 560/174 |
| 2005/0106689 A1 | 5/2005 | Braun et al. | |
| 2007/0191632 A1 * | 8/2007 | Braun | 560/227 |
| 2009/0326242 A1 | 12/2009 | Pazenok et al. | |
| 2010/0121095 A1 | 5/2010 | Pazenok et al. | |
| 2011/0009642 A1 | 1/2011 | Pazenok | |
| 2011/0028735 A1 | 2/2011 | Pazenok et al. | |
| 2011/0054183 A1 | 3/2011 | Reichert et al. | |

FOREIGN PATENT DOCUMENTS

| | | |
|---|---|---|
| DE | 1158490 | * 12/1963 |
| DE | 1158490 B | 12/1963 |
| DE | 3729106 A1 | 3/1989 |
| EP | 0082252 A1 | 6/1983 |
| EP | 0325273 A1 | 7/1987 |
| EP | 0508660 A1 | 10/1992 |
| EP | 0694526 A1 | 1/1996 |
| EP | 1038861 A1 | 9/2000 |
| EP | 1065202 A1 | 1/2001 |
| EP | 1201616 A2 | 5/2002 |
| EP | 1458670 A1 | 9/2004 |
| EP | 1682515 A1 | 7/2006 |
| EP | 2057126 A2 | 5/2009 |
| EP | 2100883 A1 | 9/2009 |
| EP | 2114855 A2 | 11/2009 |
| EP | 213341 A1 | 12/2009 |
| EP | 2285779 A1 | 2/2011 |
| GB | 931689 A | 7/1963 |
| JP | 62148482 A | 7/1987 |
| JP | 63095240 A | 4/1988 |
| JP | 11322663 A | 11/1999 |
| JP | 20000119234 A | 4/2000 |
| JP | 20000178259 A | 6/2000 |
| JP | 20010174997 A | 6/2001 |
| JP | 20010322983 A | 11/2001 |
| JP | 20010335567 A | 12/2001 |
| JP | 20010335570 A | 12/2001 |
| JP | 20010342180 A | 12/2001 |
| JP | 20010342183 A | 12/2001 |
| JP | 20010348378 A | 12/2001 |
| JP | 20020170219 A | 6/2002 |
| JP | 20060160713 A | 6/2006 |
| JP | 20090215194 A | 9/2009 |
| JP | 20090227643 A | 10/2009 |
| JP | 20100116334 A | 5/2010 |
| WO | WO 9625377 A1 | 8/1996 |

(Continued)

OTHER PUBLICATIONS

Jagodzinska et al., Tetrahedron 63 (2007) 2042-2046.*

(Continued)

*Primary Examiner* — Karl J Puttlitz
(74) *Attorney, Agent, or Firm* — Beatrice C. Ortego

(57) ABSTRACT

Esters of 4-fluorosubstituted 3-oxo-alcanoic acids can be prepared by addition reaction of ketene with the respective acid chloride, subsequent esterification and hydrodechlorination. Preferred reaction products are esters of 4,4-difluoro-3-oxo-butanoic acid.

15 Claims, No Drawings

FOREIGN PATENT DOCUMENTS

| WO | WO 0149774 A2 | 7/2001 |
|---|---|---|
| WO | WO 2004076427 A1 | 9/2004 |
| WO | WO 2005003077 A1 | 1/2005 |
| WO | WO 2005085173 A1 | 9/2005 |
| WO | WO 2006005612 A1 | 1/2006 |
| WO | WO 2007074148 A1 | 7/2007 |
| WO | WO 2009021987 A1 | 2/2009 |
| WO | WO 2009138375 A1 | 11/2009 |
| WO | WO 2010022121 A1 | 2/2010 |
| WO | WO 2011003854 A1 | 1/2011 |
| WO | WO 2011003856 A1 | 1/2011 |
| WO | WO 2011003860 A1 | 1/2011 |

OTHER PUBLICATIONS

Database Caplus Chemical Abstracts Service, Columbus, Ohio, US; Database Accession No. 1964:16133, Abstract of DE 1158490.*
U.S. Appl. No. 12/999,714, filed Mar. 31, 2011, Max Braun, et al.
U.S. Appl. No. 12/999,730, filed May 23, 2011, Max Braun, et al.
U.S. Appl. No. 12/999,750, filed Apr. 7, 2011, Max Braun, et al.
Smrt, J., et al—"Reaktion des ketens IV Uber die reaktion des ketens mit saurchloriden in schwefeldioxyd", Collection of Czechoslovak Chemical Communications, 1955, vol. 20, pp. 285-289-1955; 6 pgs (including an English abstract from Chemical Abstract).
Yu, Hai, et al—"Gas-Phase and Pd-Catalyzed Hydrodehalogenation of CBrClF2, CCl2F2, CHClF2, and CH2F2", Industrial & Engineering Chemistry Research, vol. 44 (10) pp. 3442-3452; 12 pgs, 2005.
Morato, A., et al—"Characterization and catalytic properties of several KMg1—xPdxF3 with perovskite-like structures for the hydroconversion of CHClF2" Applied Catalysis B Environmental, 2003, vol. 42 (3), Elsevier, pp. 251-264; 14 pgs.
Kraft, Bradley M., et al—Aliphatic and Aromatic Carbon-Fluorine Bond Activation with Cp*2ZrH2: Mechanisms of Hydrodefluoration, Journal of the American Chemical Society, 2001, vol. 123 (44) pp. 10973-10979; 8 pgs.
Ohnishia, R., et al—"1.14 Selective Hydrogenation of CFC-12 to HFC-32 on Zr-Pd/C Catalyst", Studies in Surface Science and Catalysis 90 Acid Base Catalysis II, 1994, pp. 101-104- 1994; 5 pgs.
Kuptsova, T.S., et al—"Preparation of Fluorotoluene by reaction of methylcyclopentadiene with difluorocarbene generated from difluorochloromethane under conditions of pulsed gas compression", Russian Chem. Bull., 1991, 40, pp. 589-582; 4 pgs (provided in English language).
Ma, P. H., et al—"Production of Highly Concentrated 13C by two-stage IRMPD", Chinese Science Bulletin, 2004, vol. 35 (16) pp. 1337-1341; 6 pgs.
Michel, Dominique,—"Simple and Efficient Industrial Preparation of Various Trifluoromethyl Ketones and Derivatives", Chimia, 2004, vol. 58, No. 3, pp. 100-103; 5 pgs.
Iwata , S., et al—"Synthesis of (trifluoromethyl)pyrazoles via 1,3-dipolar cycloaddition reaction and their derivation to photochromic fulgides", The Chemical Society of Japan, Nihon Kagaku Kaishi, 1992, No. 10, pp. 1144-1147, 5 pgs; Special Article summary in English provided on p. 1147.
Denisov, L.K., et al—Synthesis and generation characteristics of series of 7-aminocoumarins, Izvestiya timiyazevskoi sel'skokhozaitvennoi akadmi, 1984, (4), pp. 149-152; 5 pgs; Summary in English provided on p. 152.
Said, A.—New organic fine chemicals—tools for life science. Speciality Chemicals Magazine, 1984; 4(4), pp. 4, 6, 8, 10, 12-13; 7 pgs.
Kamalov, G.L., et al—Correlation Between Electronic Structure Parameters and Keto-Enol Equilibrium Constants for Substituted Acetoacetate Esters, Translation by Teoreticheskaya i Eksperimental'naya Khimiya, 16 (3) 377-379, 1980; 1981 Plenum Publishing Corporation, pp. 294-295; 2 pgs.
Kamalov, G.L., et al—"Steroechemical features of the reduction of a series of β- and γ-dicarbonyl compounds", Journal Voprosy Stereokhimii, 1977, (6) 106-111; 9 pgs; Summary in English provided on p. 111.
Loos, H., et al—"Study of Keto-Enol Equilibrium Trihalo Acetoacetic Esters"; Bulletin des Societes Chimiques Beiges, 1959, 68, pp. 129-138; 10 pgs; Summary in English provided on first page.

* cited by examiner

PROCESS FOR THE PREPARATION OF ESTERS OF 4-FLUOROSUBSTITUTED 3-OXO-ALCANOIC ACIDS

CROSS-REFERENCE TO RELATED APPLICATIONS

The present application is a U.S. national stage application under 35 U.S.C. §371 of International Application No. PCT/EP2008/060674 filed Aug. 14, 2008, which claims the benefit of European application EP 07114439.8 filed Aug. 16, 2007, the whole content of the previously cited applications being herein incorporated by reference for all purposes.

The invention concerns a process for the preparation of esters of 4-fluorosubstituted 3-oxo-alcanoic acids by addition of fluorochloroalkyl carboxylic acid chlorides to ketene, esterification and hydrodechlorination. Specifically, the invention concerns a process for the preparation of esters of 4,4-difluoro-3-oxo-butanoic acid by addition of difluorochloroacetyl chloride to ketene, esterification and subsequent reduction.

Esters of 4,4-difluoro-3-oxo-butanoic acid, especially the ethyl ester, are building blocks in chemical synthesis. These esters are useful for preparing 3-difluoromethyl-4-pyrazole-carboxylic acid esters which are intermediates for the manufacture of pyrazole carboxanilide fungicides. The preparation of such fungicides is described in U.S. Pat. No. 5,498,624 as cited in WO 2006/005612. Esters of 4,4-difluoro-3-oxo-butanoic acid are condensed with ethyl orthoformate and acetic anhydride, and the reaction product is reacted with methylhydrazine. The resulting pyrazole carboxylic acid ester is then further reacted to finally obtain the fungicide.

Esters of 4-fluorosubstituted 3-oxo-alcanoic acids, for example, 5,5,5-trifluoro-4-fluoro-3-oxo-pentanoic acid, are suitable as solvents.

Known methods to prepare esters of 4,4-difluoro-3-oxo-alcanoic acid are described in the following by the example of esters of 4,4-difluoro-3-oxo-butanoic acid. The methyl and ethyl esters of 4,4-difluoro-3-oxo-butanoic acid can be prepared by condensation with acetic acid esters under basic conditions. An alternative route is described in EP-A0 694526. Polyfluorocarboxylic acid chlorides or anhydrides are reacted with a carboxylic acid chloride in the presence of a tertiary amine, e.g. pyridine. Then, esterification is performed with an alcohol, for example, methanol or ethanol. Drawback is the low yield in case of difluoroacetoacetates.

Subject of the present invention is to provide a technically and economically advantageous process for the preparation of esters of 4-fluorosubstituted 3-oxo-alcanoic acids, and especially of esters of 4,4-difluoro-3-oxo-butanoic acid. This object is achieved by the process of the present invention.

According to the broadest aspect of the present invention, esters of 4-fluorosubstituted 3-oxo-alcanoic acids are prepared by the reaction of compounds of formula (I)

RCFClC(O)Cl    (I)

wherein R is $C_2F_5$, $CF_3$ or F, with ketene forming an adduct, reaction of the adduct in an esterification step to form the respective ester, and subsequent hydrodechlorination to form a compound of formula (II)

RCFHC(O)CH$_2$C(O)OR$^1$    (II)

wherein R has the meaning given above and $R^1$ is an alkyl group with 1 to 4 carbon atoms, or an alkyl group with 1 to 4 carbon atoms substituted by 1 or more fluorine atoms. Preferably, $R^1$ is methyl, ethyl or propyl.

The invention will now be further explained in view of the most preferred aspect of the present invention, namely the preparation of esters of 4,4-difluoro-4-chloro-3-oxobutanoic acid from difluorochloroacetyl chloride—i.e. the compound of formula (I) wherein R is F—and ketene. According to this especially preferred process of the present invention, in an addition step, difluorochloroacetylchloride is reacted with ketene to form 4,4-difluoro-4-chloro-3-oxobutanoyl chloride which then is reacted in an esterification step into the respective 4,4-difluoro-4-chloro-3-oxo-butanoic acid ester which, in a reduction step, is reduced to form the respective ester of 4,4-difluoro-3-oxo-butanoic acid.

The addition step can be performed in the gas phase or in the liquid phase. Preferably, the pressure is selected so that the gaseous ketene is introduced into the liquid difluorochloro-acetyl chloride. The temperature is preferably in the range of −50° C. to +60° C. Preferably, the pressure corresponds to the ambient pressure, but it can be higher than ambient pressure. Preferably, the pressure is equal to or lower than 5 bars (abs).

The molar ratio between difluorochloroacetyl chloride and ketene preferably lies in a range from 1:0.95 to 1:2. If desired, even more ketene can be applied.

If desired, the addition reaction can be performed in an aprotic organic solvent, for example, in an aliphatic or aromatic hydrocarbon, or a halogenated hydrocarbon, e.g. in a chlorinated hydrocarbon.

In one embodiment, the formed adduct is isolated from the reaction mixture, for example, by distillation, and the isolated product is then further reacted in the esterification step. In another embodiment, the reaction mixture is directly introduced into the esterification step without isolation of the adduct.

The esterification can be performed in any known manner. A very simple embodiment provides for the reaction of the acid chloride with the respective alcohol in the absence or the presence of a base.

The esterification step is preferably performed in the liquid phase. Preferably, the pressure is equal to ambient pressure. It also may be above ambient pressure, e.g. up to 5 bars (abs).

The molar ratio between the acid chloride and the alcohol preferably lies in a range from 1:0.8 to 1:1.5.

If desired, the addition reaction can be promoted by bases, for example, tertiary amines. If a base is added, it is advisable to cool the reaction mixture. Alternatively, the esterification can be performed in the presence of onium salts as described in U.S. Pat. Nos. 6,525,213 and 5,405,991. The advantage of this kind of reaction is that an ester phase may separate which makes isolation very easy. If no base is applied, it is advantageous to remove HCl which is a reaction product from the reaction mixture. This can be achieved by applying reduced pressure, passing inert gas through the reaction mixture, for example, nitrogen, argon or even dry air, or by heating the reaction mixture.

Finally, the CF$_2$Cl group is reduced to a CF$_2$H group. This can be achieved y known methods. A very simple and preferred method is the reduction with metals, e.g. zinc. The reaction can be performed as described in WO 2005/085173. The chlorine-containing compound is reacted preferably with 0.9 to 2.1 equivalents of metallic zinc per chlorine atom to be substituted by a hydrogen atom. An alcohol is present as proton source. Advantageously, the alcohol corresponds to the alcohol of the ester group of the butanoic acid ester. The alcohol may be present in excess and then serve as a solvent. If desired, other solvents may be present, for example, aprotic organic solvents, for example, the ester of the alcanoic acid produced in an earlier batch, or, in this preferred embodiment, respective esters of 4,4-difluoro-4-chloro-3-oxobutanoic acid produced in an earlier batch.

The difluorochloroacetyl chloride which is applied in the addition step is a commercial product. A preferred method to produce it comprises a step of photochemical oxidation of 1,1-difluoro-1,2,2-trichloroethane with oxygen in the presence or absence of promoters of the reaction, for example, chlorine. According to U.S. Pat. No. 5,545,298, the photo oxidation can be performed in the absence of chlorine under irradiation through quartz glass. If desired, the reaction can be performed without pressurization. According to U.S. Pat. No. 5,569,782 photo oxidation is performed in the absence of chlorine under exposure with light of a wavelength equal to or shorter than 290 nm. The undesired wavelengths can be cut off by applying borosilicate glass. Alternatively, radiation sources could be applied which emit radiation essentially only in the desired range. If desired, the oxidation reaction could be performed under unpressurized conditions. The reaction can also be performed under pressure. Fluorinated carboxylic acid chlorides which are alpha-substituted by a chlorine atom can be prepared analogously from respective starting compounds.

The chlorofluorosubstituted starting compounds needed for the photo oxidation reaction can be prepared according to known methods. For example, 1,1,-difluoro-1,2,2-dichloroethane is commercially available; it can be prepared by the reaction of tetrachloroethylene and HF in the presence of catalysts, e.g. tantalum halides or antimony halides, especially antimony (V) chloride or its fluorination products.

The method according to the present invention provides a cheap, technically feasible process for the preparation of esters of 4,4-difluoro-3-oxo-butanoic acid and its homologues.

The following example is intended to further explain the invention without limiting it.

EXAMPLE

Preparation of Esters of 4,4-difluoro-3-oxo-butanoic Acid 1,1,-difluoro-1,2,2-trichloroethane from a commercial source is reacted with oxygen in the absence of chlorine in an apparatus with borosilicate glass as filter for light with a wavelength of lower than around 290 nm under the conditions indicated in U.S. Pat. No. 5,569,782.

HCl is removed, and without separate isolation of the formed chlorodifluoroacetyl chloride, the reaction product is reacted with ketene by passing ketene through the liquid acid chloride, dissolved in methylene chloride. The reaction mixture is cooled and kept in a range of −10 to −30° C. Afterwards, lightboiling substances are removed, and the raw difluorochloroacetylacetic acid chloride is esterified with ethanol in the absence of a base. HCl is removed, and the resulting raw product is reacted with zinc powder in the presence of ethanol as described in WO 2005/085173. The resulting ethyl ester of 4,4-difluoro-3-oxo-butanoic acid is isolated by distillation.

The invention claimed is:

1. A process for the preparation of esters of 4-fluorosubstituted 3-oxo-alcanoic acids, comprising
an addition reaction of compounds of formula (I)

RCFClC(O)Cl  (I)

wherein R is $C_2F_5$, $CF_3$ or F, with ketene forming an adduct of the following formula:

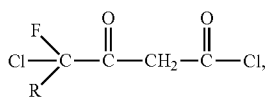

a reaction of the adduct in an esterification step to form the respective ester, and
a subsequent one-step hydrodechlorination of the ester to form a compound of formula (II)

RCFHC(O)CH$_2$C(O)OR$^1$  (II)

wherein R has the meaning given above, and $R^1$ is an alkyl group with 1 to 4 carbon atoms, or an alkyl group with 1 to 4 carbon atoms substituted by 1 or more fluorine atoms.

2. The process according to claim 1 wherein R is F.

3. The process according to claim 1 wherein $R^1$ is methyl, ethyl or propyl.

4. The process according to claim 1 wherein the esterification step is performed in the absence of a base or phase-separating agents.

5. The process according to claim 1 wherein the compound RCFClC(O)Cl of formula (I) is prepared by photo oxidation of RCFClCHCl$_2$ with oxygen wherein R is $C_2F_5$, $CF_3$ or F.

6. The process according to claim 1 wherein the esterification is performed with an alcohol, and the hydrodechlorination is performed by reaction of the ester with zinc in the presence of the same alcohol which is applied in the esterification step.

7. The process according to claim 6 wherein the alcohol applied in the esterification and hydrodechlorination steps is ethanol.

8. The process according to claim 3 wherein $R^1$ is ethyl.

9. The process according to claim 1 wherein the formed adduct is isolated from the addition reaction mixture, and the isolated product is then further reacted in the esterification step.

10. The process according to claim 1 wherein the reaction mixture containing the adduct is directly introduced into the esterification step without isolation of the adduct.

11. The process according to claim 1 wherein difluorochloroacetyl chloride CF$_2$ClC(O)Cl which is the compound of formula (I) wherein R is F is reacted with ketene to form 4,4-difluoro-4-chloro-3-oxobutanoyl chloride which then is reacted in the esterification step into 4,4-difluoro-4-chloro-3-oxo-butanoic acid ester, and wherein the hydrodechlorination step is a reduction which forms the respective ester of 4,4-difluoro-3-oxo-butanoic acid.

12. The process according to claim 11 wherein the molar ratio between difluorochloroacetyl chloride and ketene is in a range from 1:0.95 to 1:2.

13. The process according to claim 1 wherein the hydrodechlorination step is a reduction carried out in the presence of metallic zinc with 0.9 to 2.1 equivalents of metallic zinc per chlorine atom to be substituted by a hydrogen atom.

14. The process according to claim 1 wherein the gaseous ketene is introduced into the compound of formula (I) in liquid form.

15. The process according to claim 1 wherein the formed adduct is isolated by distillation, and the isolated product is then reacted in the esterification step.

* * * * *